(12) United States Patent
Venkitasubramanian (10) Patent No.: US 9,234,064 B2
(45) Date of Patent: Jan. 12, 2016

(54) PROCESSES FOR MAKING ACRYLIC-TYPE MONOMERS AND PRODUCTS MADE THEREFROM

(75) Inventor: Padmesh Venkitasubramanian, Forsyth, IL (US)

(73) Assignee: Archer Daniels Midland Company, DeCatur, IL (US)

( * ) Notice: Subject to any disclaimer, the term of this patent is extended or adjusted under 35 U.S.C. 154(b) by 225 days.

(21) Appl. No.: 14/116,525

(22) PCT Filed: May 1, 2012

(86) PCT No.: PCT/US2012/035981
§ 371 (c)(1),
(2), (4) Date: Nov. 8, 2013

(87) PCT Pub. No.: WO2012/154450
PCT Pub. Date: Nov. 15, 2012

(65) Prior Publication Data
US 2014/0206831 A1    Jul. 24, 2014

Related U.S. Application Data

(60) Provisional application No. 61/484,834, filed on May 11, 2011.

(51) Int. Cl.
| | |
|---|---|
| *C07C 67/00* | (2006.01) |
| *C07D 317/00* | (2006.01) |
| *C08F 220/14* | (2006.01) |
| *C07C 67/343* | (2006.01) |
| *C07C 67/39* | (2006.01) |
| *C07D 317/12* | (2006.01) |
| *C07C 45/52* | (2006.01) |
| *C07C 45/65* | (2006.01) |
| *C08F 20/06* | (2006.01) |
| *C07C 51/235* | (2006.01) |
| *C07C 51/16* | (2006.01) |
| *C07C 67/40* | (2006.01) |

(52) U.S. Cl.
CPC .............. *C08F 220/14* (2013.01); *C07C 45/52* (2013.01); *C07C 45/65* (2013.01); *C07C 51/16* (2013.01); *C07C 51/235* (2013.01); *C07C 67/343* (2013.01); *C07C 67/39* (2013.01); *C07C 67/40* (2013.01); *C07D 317/12* (2013.01); *C08F 20/06* (2013.01)

(58) Field of Classification Search
CPC ........ C07C 45/52; C07C 45/65; C07C 67/39; C07C 67/343; C07D 317/12
USPC ......................... 560/208; 562/538; 526/328.5
See application file for complete search history.

(56) References Cited

U.S. PATENT DOCUMENTS

| | | | | |
|---|---|---|---|---|
| 4,336,403 A * | 6/1982 | Merger | ................... | C07C 69/54 |
| | | | | 502/215 |
| 4,496,770 A * | 1/1985 | Duembgen | ............. | C07C 45/75 |
| | | | | 568/461 |
| 4,638,085 A * | 1/1987 | Broecker | ............... | B01J 23/628 |
| | | | | 502/303 |
| 4,892,856 A * | 1/1990 | Kawajiri | ................ | B01J 23/002 |
| | | | | 502/247 |
| 6,479,713 B1 * | 11/2002 | Werpy | ..................... | B01J 23/36 |
| | | | | 568/861 |

OTHER PUBLICATIONS

Diaz et al. Homogeneous Oxidation Reactions of Propanediols at Low Temperatures. ChemSusChem, 2010, 3, 1063-1070.*
Azzouz et al. Vapor phase aldol condensation over fully ion-exchanged montmorillonite-rich catalysts. Applied Catalysis A: General, 241 (2003), 1-13.*

* cited by examiner

*Primary Examiner* — Sikarl Witherspoon
(74) *Attorney, Agent, or Firm* — William B. Miller (57) ABSTRACT

Presently disclosed are processes for making acrylic acid and methacrylic acid along with their respective esters, from alkylene glycols such as ethylene glycol and propylene glycol. In particular, biobased acrylic acid and acrylic acid esters, methacrylic acid and methacrylic acid esters can be made starting with bioderived glycols from the hydrogenolyzis of glycerol, sorbitol and the like.

7 Claims, 5 Drawing Sheets

Fig. 1

Propylene glycol Process

PROCESSES FOR MAKING ACRYLIC-TYPE MONOMERS AND PRODUCTS MADE THEREFROM

The present application is in the field of art relating to acrylic acid and acrylate (including alkylacrylate) ester monomers and to the methods by which such monomers are made, and further relates to acrylic acid and acrylate ester compositions incorporating these monomers.

Acrylic acid monomers and acrylate ester monomers, such as methacrylate ester monomers, are highly reactive, common precursors to many essential polymers. Acrylic acid is commonly synthesized from acrolein through the catalytic oxidation of propylene, which is a product of ethylene and gasoline production. Methacrylate esters are commonly synthesized from acetone and hydrogen cyanide.

Acrylic acid monomers are materials which easily polymerize to form acrylic resins. Acrylic acids can also be esterified to form acrylic acid esters. Both acrylic acid and acrylic acid esters self-polymerize, and also combine with other comonomers such as acrylamides, acrylonitrile, vinyl, styrene, and butadiene to create polymers, as needed for a particular end use. Acrylic polyacrylate homopolymers are used in the manufacture of superabsorbent polymers (SAPs), thickeners, detergents and dispersants, while acrylic heteropolymers are used to manufacture a broad range of plastics, coatings, adhesives, elastomers, polishes, and paints. Methacrylate esters are polymerized to make polymethyl methacrylate acrylic plastic homopolymers, and can also polymerize with other monomers to form copolymers useful as acrylic sheets, molding compounds, resins and latexes for use in coatings, adhesives, waxes, polishes, and thermosetting automotive/appliance enamels.

Historically, acrylic acid monomers and methacrylate ester monomers have been made from certain petroleum-derived compounds. However, such petroleum-derived monomers are frequently expensive to produce and use because of fluctuations in the pricing and availability of petroleum, and are increasingly likely to remain so as petroleum reserves are reduced and new supplies prove more costly and difficult to secure. Further, in the context of methacrylate ester production, the use of hydrogen cyanide and the production of large amounts of ammonium sulfate by-product have raised concerns for process safety and byproduct disposal.

Efforts have consequently been made as well to produce acrylic acid monomers and methacrylate ester monomers from renewable sources, as a more sustainable alternative to the petroleum-based routes. For example, as related in United States Patent Application Publication No. US2009018300 to Venkitasubramanian and Bloom, bioderived glycerol may be dehydrated to give acrolein. The bioderived acrolein may then be oxidized in the same manner generally as acrolein from petroleum-based propylene, to afford acrylic acid. Alternatively, biobased acrylic acid or acrylate esters may be synthesized from biobased lactic acid or lactate esters. Bio-based lactic acid derivatives may be bio-synthesized, for example, by fermentation of a carbohydrate material. Conversion of lactic acid and lactate esters into acrylic acid and acrylate esters, respectively, may be accomplished by dehydration of the alcohol group of the lactate moiety. Suitable methods for the conversion of lactic acid and lactate esters, for example, lactic acid/lactate esters from the fermentation of carbohydrate material in the presence of ammonia, into an acrylate ester or acrylic acid are disclosed in U.S. Pat. Nos. 5,071,754 and 5,252,473. Alternatively, an extruded catalyst for producing acrylic acid by dehydrating biomass lactic acid is taught in Chinese Patent Application Publication Nos. CN101462069A (published Jun. 24, 2009) and CN101474572A (published Jul. 7, 2009).

The new methods with which the present application is concerned make use of alkylene glycols (such as ethylene glycol or propylene glycol) to provide one or more of the desired acrylic acid and its esters, and/or methacrylic acid and esters of methacrylic acid. In one refinement, alkylene glycols as may be produced from bioderived (biologically sourced) glycerol, sugars or sugar alcohols are used to provide one or more of bioderived acrylic acid, bioderived methacrylic acid and the bioderived esters of acrylic acid and methacrylic acid, in any combination.

In one aspect, a process is provided whereby propylene glycol is converted to products including acrylic acid especially. Propylene glycol (CAS #57-55-6) is first subjected to chemical dehydration to form propanal (propionaldehyde, CAS #123-38-6). The propanal is subjected to desaturation to form propenal (CAS #107-02-8). The propenal is then subjected to oxidation to form the acrylic acid (CAS #79-10-7). In the analogous process starting from ethylene glycol (CAS #107-21-1), the ethylene glycol is dehydrated to form acetaldehyde (ethanal, CAS #75-07-0), which undergoes an aldol condensation with formaldehyde (CAS #50-00-0, methanal) to provide 3-hydroxypropanal. 3-hydroxypropanal undergoes rearrangement to form acrolein, and the acrolein can be oxidized to form the acrylic acid.

In a second aspect, a process is provided that is particularly directed to making a methacrylate ester from an alkylene glycol, such as propylene glycol, especially from a biobased propylene glycol. After a chemical dehydration of propylene glycol to form propanal, the propanal is subjected to aldol condensation with formaldehyde to form methacrolein (CAS #78-85-3). The methacrolein is then subjected to oxidative esterification with an alcohol to form the alkyl methacrylate ester, for example, with methanol to form methyl methacrylate (CAS #80-62-6).

In still a third aspect, an alternative process is provided for making a methacrylate ester from an alkylene glycol, especially a propylene glycol, particularly, from a biobased propylene glycol. After a chemical dehydration of propylene glycol to form propanal, the propanal is subjected to oxidative esterification with an alcohol such as methanol to form methyl propionate (CAS #554-12-1). The methyl propionate is then subjected to aldol condensation with formaldehyde to form methyl methacrylate.

In still another aspect, a process is provided for making an acrylate ester (CAS #96-33-3) from ethylene glycol, whereby ethylene glycol is dehydrated to acetaldehyde. Acetaldehyde undergoes an aldol condensation reaction with formaldehyde to provide 3-hydroxypropanal, which rearranges to provide acrolein. Acrolein can then be reacted with methanol in the presence of an esterification catalyst to yield methyl acrylate.

Still other aspects and features of the new methods of manufacture and of the products and compositions resulting from the new methods of manufacture will be evident from the drawings and the more detailed description below of various, non-limiting and illustrative embodiments.

FIG. 5 also shows how ethanol can be converted to methyl acrylate or acrylic acid.

Various embodiments are hereafter described to illustrate the contributions made herein to the art, as more particularly defined by the claims below. It will be understood of course that these embodiments are offered for illustrative purposes only, and those skilled in the art will most certainly be able to develop still other embodiments that nevertheless fall within the scope and spirit of the inventive subject matter defined in the claims following.

Figure 1:
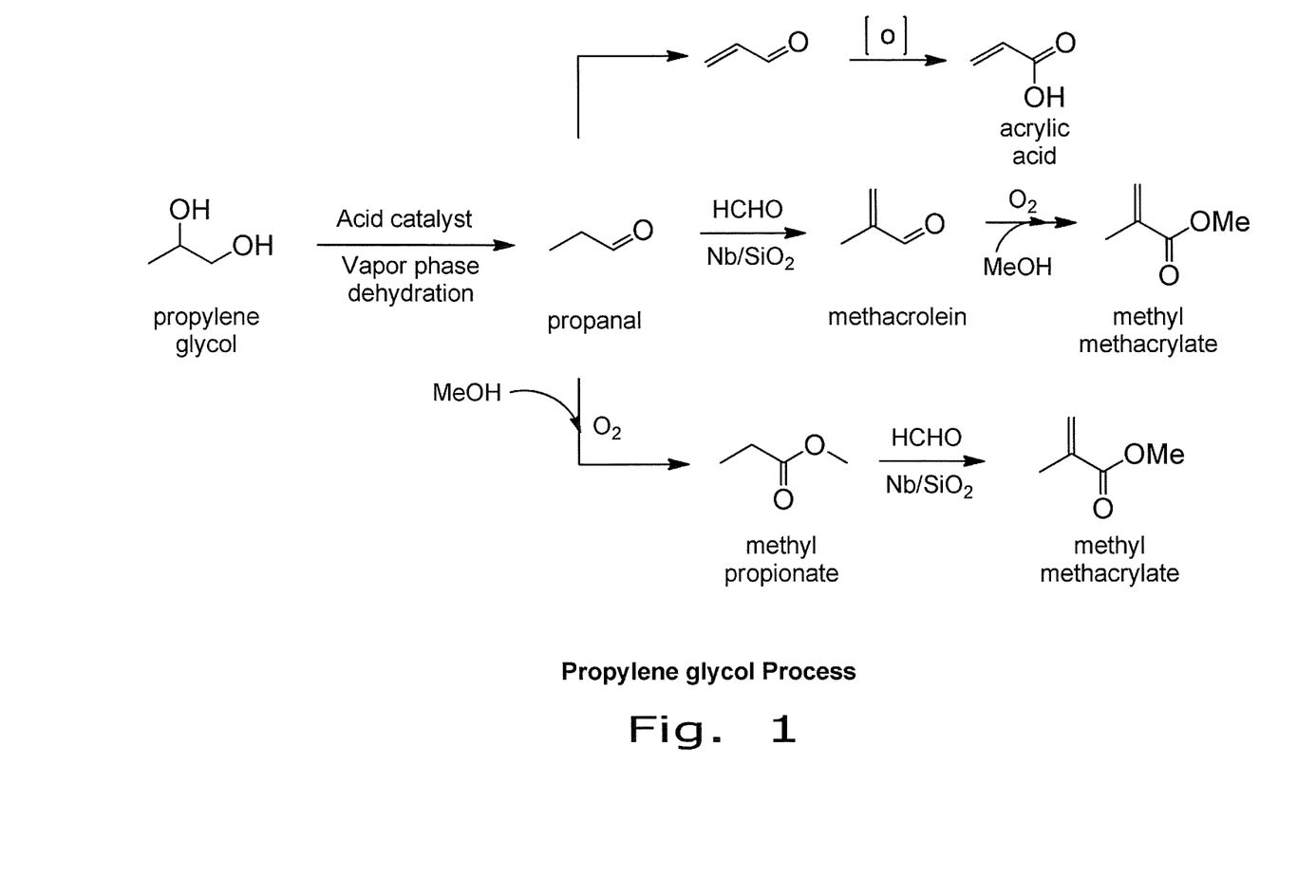
FIG. 1 schematically illustrates processes for making an acrylic acid product, for making a methyl methacrylate product via methacrolein, and for making a methyl methacrylate product via methyl propionate from propylene glycol.

With this understanding, in FIG. 1 a process is schematically illustrated for making an acrylic acid product from propylene glycol, and a methyl methacrylate product from propylene glycol via methacrolein, and a methyl methacrylate product from propylene glycol via methyl propionate. It will be appreciated, of course, that while FIG. 1 schematically shows all three conversions, some subset of these (including any two in combination or any of the three conversions individually) may also be practiced as desired.

The propylene glycol may be bioderived, having been produced from a biobased glycerol according to any of the various known processes for accomplishing this end, and/or having been produced from sugars or sugar alcohols according to any of the various known processes for making propylene glycol starting with such materials. Numerous methods for making a bioderived propylene glycol from glycerol, from sugars and sugar alcohols are described in the literature. A representative sampling of patented or published methods includes, for example, in U.S. Pat. Nos. 6,479,713; 6,841,085; and 7,038,094 (all to Werpy et al.); U.S. Pat. No. 6,080,898 to Drent et al.; U.S. Pat. No. 7,790,937 to Henkelmann et al.; U.S. Pat. No. 7,816,567 to Suppes et al.; U.S. Pat. No. 7,767,867 to Cortright; U.S. Pat. No. 4,430,253 to Dubeck et al; U.S. Pat. No. 5,354,914 to Gubitosa et al; U.S. Pat. No. 5,210,335 to Schuster et al; U.S. Pat. No. 5,214,219 to Casale et al; U.S. Pat. No. 5,616,817 to Schuster et al; U.S. Pat. No. 6,291,725 to Chopade et al; and U.S. Pat. No. 7,619,124 to Miller et al., as well as PCT Patent Application Publications No. WO 2005/051874 (Crabtree et al.); WO 2009/151021A1 (Yoshimura et al.); WO 2010/119351A1 (Hronec); and WO 2010/094769A1 (Maurer et al.).

Where biobased glycerol is selected to serve as a feedstock, this is presently available from the transesterification reaction of lower alkanols with higher fatty acid triglycerides, to yield lower alkyl esters of higher fatty acids and a substantial glycerol co-product. Glycerol is also available as a co-product of the hydrolysis reaction of water with higher fatty acid triglycerides to yield soap and glycerol. The higher fatty acid triglycerides may derive from animal or vegetable (plant) sources, or from a combination of animal and vegetable sources as well known, and a variety of processes have been described or are known.

In the context of vegetable oil-based biodiesel production and soap making, all sorts of vegetable oils have been combined with the lower aliphatic alcohols or water. Preferred vegetable oils include, but are not limited to, soybean oil, linseed oil, sunflower oil, castor oil, corn oil, canola oil, rapeseed oil, palm kernel oil, cottonseed oil, peanut oil, coconut oil, palm oil, tung oil, safflower oil and derivatives, conjugated derivatives, genetically-modified derivatives and mixtures thereof. As used herein, a reference to a vegetable oil includes all its derivatives as outlined above. For instance, the use of the term "linseed oil" includes all derivatives including conjugated linseed oil.

In addition, a biobased glycerol is available as a product of the hydrogenolysis of sorbitol, as described for example in U.S. Pat. No. 4,366,332, issued Dec. 28, 1982.

Five and six carbon sugars and sugar alcohols may also be used as a biobased feedstock for producing a bioderived propylene glycol. Sugars containing five carbon chains, such as ribose, arabinose, xylose and lyxose, and corresponding five carbon chain sugar alcohols such as xylitol and arabinitol, are among the materials contemplated in U.S. Pat. No. 7,038,094 to Werpy et al., for example, as are six carbon sugars such as glucose, galactose, maltose, lactose, sucrose, allose, altrose, mannose, gulose, idose and talose and six carbon chain sugar alcohols such as sorbitol. Some of these carbohydrate-based feedstocks are commercially available as pure or purified materials. These materials may also be obtained as side-products or even waste products from other processes, such as corn processing. The sugar alcohols may also be intermediate products produced in the initial stage of hydrogenating a sugar.

The feedstock(s) and method(s) to be preferred for producing a bioderived propylene glycol will, it is expected, depend for example on whether glycerol is more readily accessible as a feedstock or whether the sugars and sugar alcohols just discussed are more readily accessible. In any event, numerous options are documented in the art for preparing propylene glycol from biobased feedstocks inclusive of glycerol and the sugars and sugar alcohols, and those skilled in the art will be well able to determine which feedstock and method will most economically produce a bioderived propylene glycol for further processing according to the present invention.

Bioderived propylene glycol, such as propylene glycol from glycerol or from five and six carbon sugars and sugar alcohols, may contain ethylene glycol. For example, U.S. Pat. No. 6,479,713 teaches that ethylene glycol may be present in the product of the hydrogenolysis of 6 carbon sugars, 6 carbon sugar alcohols, glycerol, 5 carbon sugars, 5 carbon sugar alcohols, lactate or lactic acid, such as in the hydrogenolysis of sorbitol to propylene glycol. The propylene glycol and ethylene glycol may be separated, such as by distillation, but as demonstrated and discussed in greater detail below a mixed, bioderived or biobased alkylene glycol feed may also be used to produce the contemplated acrylic-variety or -type monomers.

Parenthetically, as these terms are used interchangeably herein, we intend by "biologically derived", "bioderived" or "biobased" that these will be understood as referring to materials whose carbon content is shown by ASTM D 6866, in whole or in significant part (for example, at least 20 percent or more), to be derived from or based upon biological products or renewable agricultural materials (including but not limited to plant, animal and marine materials) or forestry materials. In this respect ASTM Method D6866, similar to radiocarbon dating, compares how much of a decaying carbon isotope remains in a sample to how much would be in the same sample if it were made of entirely recently grown materials. The percentage is called the biobased content of the product. Samples are combusted in a quartz sample tube and the gaseous combustion products are transferred to a borosilicate break seal tube. In one method, liquid scintillation is used to count the relative amounts of carbon isotopes in the carbon dioxide in the gaseous combustion products. In a second method, 13C/12C and 14C/12C isotope ratios are counted (14C) and measured (13C/12C) using accelerator mass spectrometry. Zero percent 14C indicates the entire lack of 14C atoms in a material, thus indicating a fossil (for example, petroleum based) carbon source. One hundred percent 14C, after correction for the post-1950 bomb injection of 14C into the atmosphere, indicates a modern carbon source. ASTM D 6866 effectively distinguishes between biobased materials and petroleum derived materials in part because isotopic fractionation due to physiological processes, such as, for example, carbon dioxide transport within plants during photosynthesis, leads to specific isotopic ratios in natural or biobased compounds. By contrast, the 13C/12C carbon isotopic ratio of petroleum and petroleum derived products is different from the isotopic ratios in natural or bioderived compounds due to different chemical processes and isotopic fractionation during the generation of petroleum. In addition, radioactive decay of the unstable 14C carbon radioisotope leads to different isotope ratios in biobased products compared to petroleum products.

In the process of FIG. 1, propylene glycol is subjected to an elimination reaction comprising chemical dehydration. Water is removed from propylene glycol to yield propanal. Because water is a poor leaving group, the dehydration reaction may be accelerated with a catalyst, such as an acid catalyst. An example of a process of this character can be found in Applied Catalysis A: General 366 (2009) 304-308, wherein dehydration of propylene glycol over a silica-supported silicotungstic acid catalyst proceeded with 100% conversion to propanal at a propanal selectivity level greater than 93 mol %. Other suitable acid catalysts comprise tungstated zirconia, strong acid ion exchange acid catalyst, mineral acids, trifluoroacetic acid, zeolites, triflic acids, methanesulfonic acid, and combinations of any thereof.

Other methods for converting propylene glycol to propanal have been published and may be used, in the alternative. Enzymatic routes have been elucidated using dioldehydrase (Frey, P. et al., J. Biological Chemistry (1966), 241(11), 2732-3; Zagalak, B. et al., J. Biological Chemistry (1966), 241(13), 3028-35. Abeles R. et al., J. American Chemical Society (1971), 93(5), 1242-51); glycerol dehydratase ("Preparation of *Lactobacillus reuteri* glycerol dehydratase and its use for preparation of aldehydes", Zheng, Y., et al. Faming Zhuanli Shenqing Gongkai Shuomingshu (2010), Chinese Patent Application No. CN 2009-10153309, dated 20091015); and propanediol dehydratase (United States Patent Publication No. 2010185017A). As well, other catalytic approaches have been demonstrated, including using silicotungsten catalysts (Cheng, L. & Ye, X., Catalysis Letters (2009), 130(1-2), 100-107) and bivalent transition metal sulfates in supercritical water (Lehr, V., et al., Catalysis Today (2007), 121(1-2), 121-129).

Referring back to FIG. 1, the propanal (or propionaldehyde) derived from propylene glycol is converted to propenal (or acrolein) in a desaturation (or dehydrogenation) step. One published method for converting propanal to propenal is by contact with one or more oxides of As, Sb, or Bi at 100-600° C. for 0.1-100 seconds, as described in German Patent DE1154082, issued Sep. 12, 1963. An alternative route is described as dehydrogenation of saturated aldehydes over divanadyl pyrophosphate catalyst supported on weakly acidic and basic metal oxide (Japanese Patent Application JP 2003326168A, dated Nov. 18, 2003). Another alternative route is described as alpha-selenylation of saturated aldehydes followed by oxidation to form the unsaturated aldehydes (Sheng, S.-R. et al., J. Chemical Research, Synopses (2003), (5) 258-259). Desaturation may also be carried out in methods using a zeolite-supported alkali catalyst (Japanese Patent Application JP 09057108A, dated Mar. 4, 1997) or an alkali earth metal oxide catalyst (Japanese Patent No. JP 3796774B2, dated Jul. 12, 2007). A bismuth phosphomolybdate catalyst has also been described for dehydrogenation of saturated aldehydes (British Patent No. GB1124797A, issued Aug. 21, 1968).

The propenal formed from propanal is oxidized to acrylic acid by known methods, such as partial oxidation over $V_2O_5$—$P_2O_5$ catalysts, which oxidizes the aldehyde group without attacking the propenal carbon-carbon double bond (Ai, M., Applied Catalysis, 27 (1986) 167-179). Following these non-limiting steps, acrylic acid is synthesized from propylene glycol.

Referring again to FIG. 1, propanal derived from propylene glycol may also be subjected to condensation with formaldehyde (aldol condensation) to produce methacrolein. One published method wherein propanal is reacted with formaldehyde in the presence of a secondary amine at high pressure and a temperature greater than 150° C., optionally in the presence of an acid, is described in U.S. Pat. No. 4,496,770, issued Jan. 29, 1985, wherein a yield of 98.1% of theoretical yield of methacrolein was obtained in Example 1. The methacrolein is then oxidized to methacrylic acid and the methacrylic acid then esterified with methanol to form methyl methacrylate. Optionally, of course, methacrylic acid may be formed and recovered as the desired product without proceeding to the methyl methacrylate product illustrated in FIG. 1. One method wherein methacrolein is converted to methyl methacrylate by incubating the methacrolein with methanol and oxygen over a supported palladium-lead catalyst is described in U.S. Pat. No. 4,638,085, issued Jan. 20, 1987. The formaldehyde may be biobased formaldehyde obtained by the oxidation of methane obtained from aerobic fermentation, from syngas biomethanol produced from glycerine from biodiesel manufacture, or by enzymatic oxidation of biomethanol produced from glycerine by methanol dehydrogenase, Referring again to FIG. 1, propanal derived from propylene glycol may also be subjected to oxidative condensation with methanol to form methyl propionate. The methyl propionate is then oxidized to propionic acid and esterified with methanol to form methyl methacrylate. One published method for converting propanal to methyl propionate comprises incubating propanal with methanol and oxygen over a supported palladium-lead catalyst as described in U.S. Pat. No. 4,638,085, issued Jan. 20, 1987. Methyl propionate is then condensed with formaldehyde to produce methyl methacrylate. For example, a vanadium pentoxide-phosphorus pentoxide binary oxide with a phosphorus:vanadium atomic ratio of 1.06 is described in Applied Catalysis, 36 (1988) 221-230. In an alternative process, methyl propionate is then condensed with methanol over a mixture of catalysts as described in U.S. Pat. No. 4,336,403 to produce methyl methacrylate.

Figure 2:
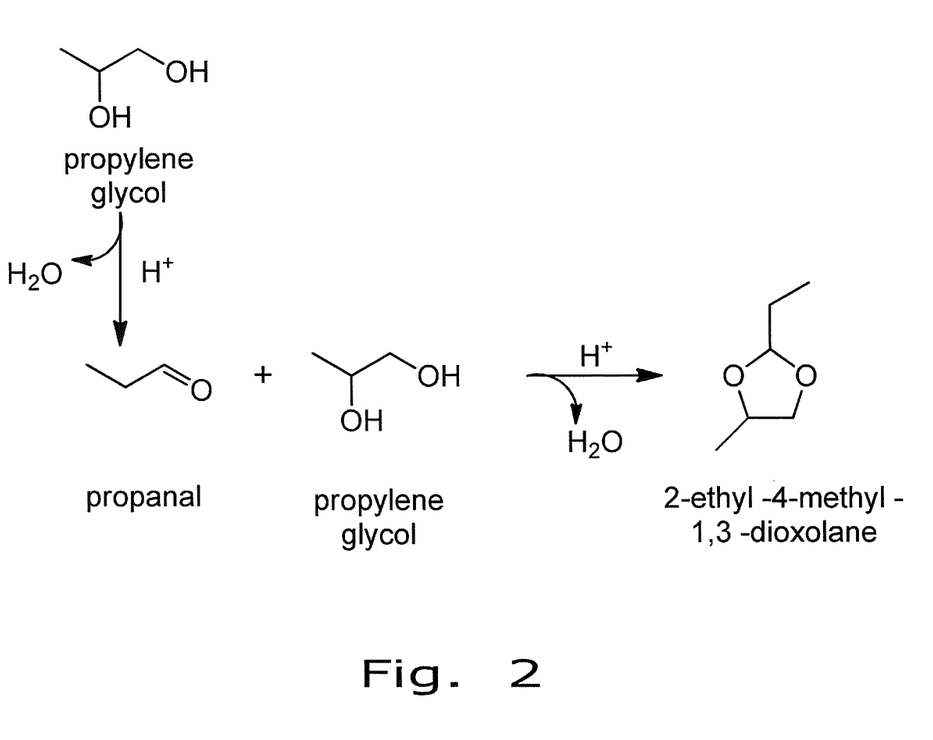
FIG. 2 schematically illustrates a process for dehydrating propylene glycol to propanal and trapping the propanal in an adduct with propylene glycol (2-ethyl-4-methyl-1,3 dioxolane).
Figure 3:
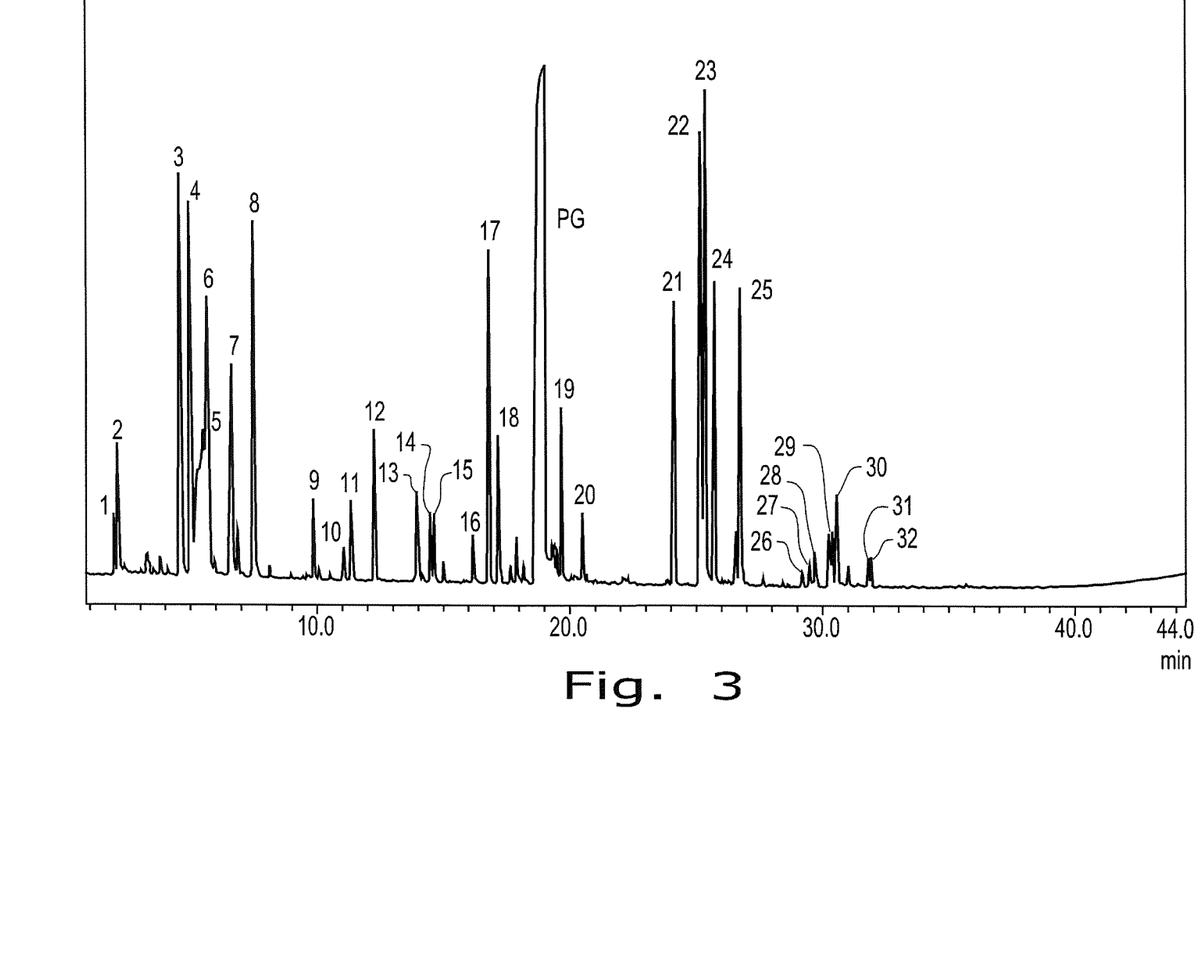
FIG. 3 presents a GC-MS chromatogram of the bottom layer formed in Example 2B. Peaks 3 and 4 are 4-methyl-2-ethyl-1,3-dioxolane.

Referring now to FIG. 2, propylene glycol (including but not being limited to biobased propylene glycol) may be subjected to catalytic dehydration to propanal in the presence of an acid, such as a mineral acid, as disclosed herein. In the reaction mixture, the propanal that is formed can then condense with propylene glycol in a dehydration reaction to form 2-ethyl-4-methyl-1,3-dioxolane. The presence of 2-ethyl-4-methyl-1,3-dioxolane, in which propanal is essentially trapped in an adduct with propylene glycol, confirms the formation of propanal as a dehydration product. Chromatograms showing the detection of 4-methyl-2-ethyl-1,3-dioxolane are presented in FIGS. 3 and 4.

Propylene glycol and ethylene glycol as non-biobased feeds are manufactured in separate and distinct processes, and accordingly would in most instances be converted separately by methods such as described herein to the desired acrylic-type monomers. However, as mentioned previously, EG can be formed as a co-product in the synthesis of biobased PG to form a mixed stream of biobased PG and EG (PG/EG mix). The amount of EG and PG in the mixed stream can vary based on different combinations of certain reaction parameters, as shown for example in U.S. Pat. No. 7,619,124. As well, the mixed glycol reaction product resulting from hydrogenolysis of glycerol to form biobased propylene glycol can be subjected to some degree of purification, such as by distillation, to remove ethylene glycol and provide a mixed glycol feed that is relatively higher in PG content. A distillate enriched in ethylene glycol but containing up to 50% propylene glycol may in this fashion be obtained and used as a PG/EG mixed feed.

In the process of the present invention, such a biobased PG/EG mix can advantageously be processed directly according to the methods described herein, without separation and purification of the PG and EG products—thus avoiding certain costs associated with conventionally sourced PG and EG streams, respectively—to form mixtures of acrylic acid and methacrylic acid. The mixtures of acrylic acid and methacrylic acid can in turn be mixed with an organic compound capable of copolymerization with a mixture of alkyl acrylate and alkyl methacrylate to form a prepolymer syrup. The prepolymer syrup can be mixed with an organic peroxide and an activator to form a polymerizable mixture, which can be cast to form a polymerized solid mass.

More particularly, a PG/EG mix can be processed to form a mixture of aldehydes. When a PG/EG mix is subjected to dehydration with a dehydration catalyst, the PG is dehydrated to propanal, and the EG is dehydrated to form acetaldehyde as outlined herein. In an embodiment, the acetaldehyde can be recovered and subjected to condensation with formaldehyde as outlined herein to produce acrolein. The acrolein may then be oxidized by partial oxidation to yield acrylic acid.

A PG/EG mix can in like manner be processed to form mixtures of acrylic acid and methacrylic acid. According to one embodiment, a PG/EG mix is subjected to dehydration with a dehydration catalyst, the PG is dehydrated to propanal, and the EG is dehydrated to form acetaldehyde as outlined herein. The mixture of propanal and acetaldehyde is subjected to condensation with formaldehyde to form a mixture of acrolein from EG and methacrolein from PG. The mixture of acrolein and methacrolein may then be oxidized by partial oxidation to yield a mixture of acrylic acid and methacrylic acid.

A PG/EG mix can alternatively be processed to form mixtures of alkyl acrylates and alkyl methacrylates. A PG/EG mix is subjected to dehydration with a dehydration catalyst, the PG is dehydrated to propanal, and the EG is dehydrated to form acetaldehyde as outlined herein. The mixture of propanal and acetaldehyde is subjected to condensation with formaldehyde to form a mixture of acrolein and methacrolein. The mixture of acrolein and methacrolein may then be reacted with methanol to form a mixture of methyl acrylate and methyl methacrylate. The mixtures of alkyl acrylate and alkyl methacrylate can be mixed with an organic compound capable of copolymerization with the mixture of alkyl acrylate and alkyl methacrylate to form a prepolymer syrup. In one embodiment, the prepolymer syrup is mixed with an organic peroxide and an activator to form a polymerizable mixture, which can be cast to form a polymerized solid mass. Mixtures of alkyl acrylate and alkyl methacrylate prepared together from an PG/EG mix can also be subjected to anionic polymerization with core monomers and incorporated into star polymers suitable for addition to synthetic or mineral oil as a lubricating oil additive.

Figure 5:
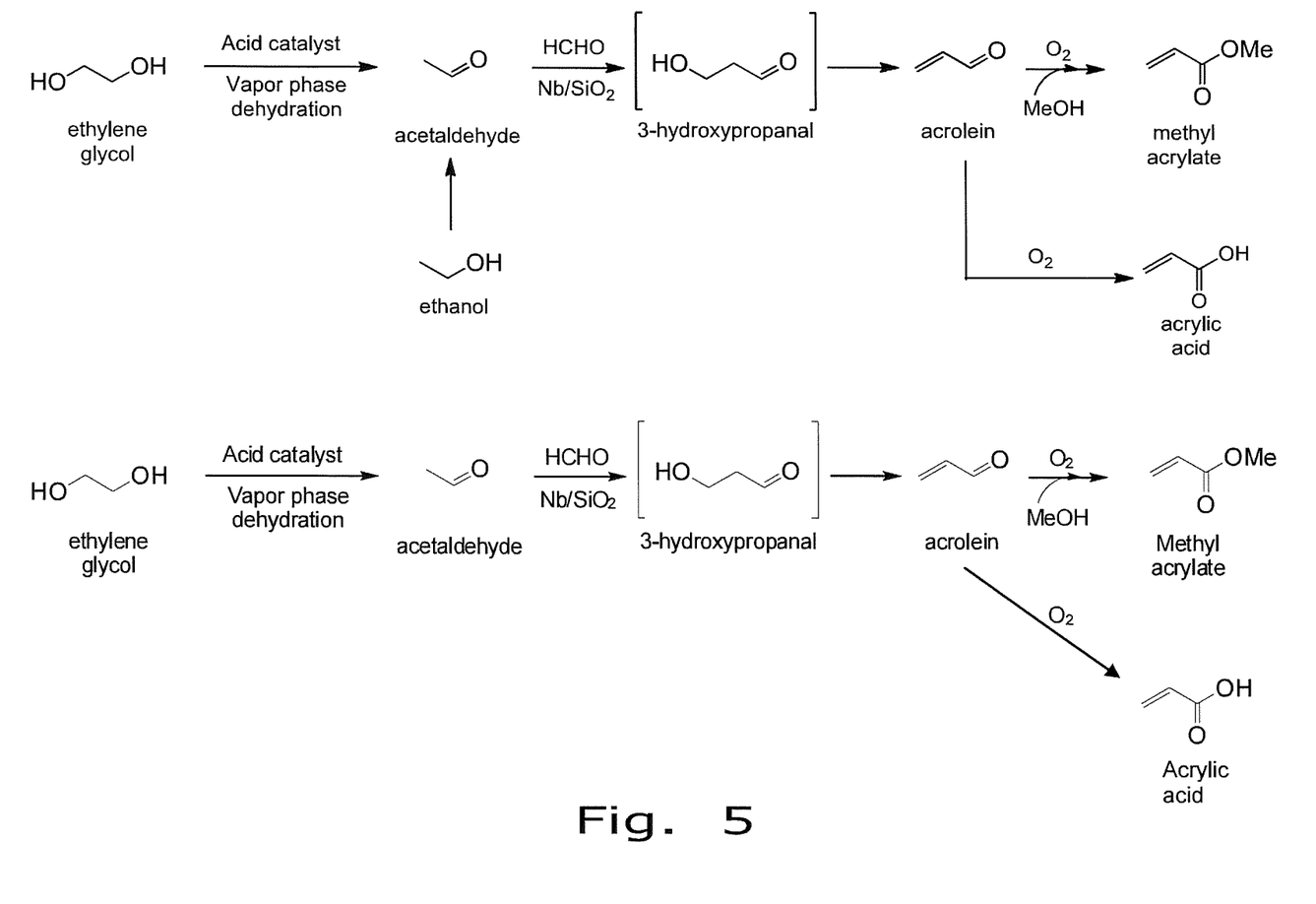
FIG. 5 schematically illustrates a process for conversion of ethylene glycol to methyl acrylate or acrylic acid.

Referring now to FIG. 5, ethylene glycol as a standalone feed or as a component of a mixed alkylene glycols feed may be converted to methyl acrylate or acrylic acid. Conversion may be accomplished as indicated, first by subjecting ethylene glycol to vapor-phase dehydration over an acid catalyst to form acetaldehyde. The acetaldehyde may be subjected to hydroformylation to form 3-hydroxypropanal, which rearranges to form acrolein. Acrolein can then be converted through reaction with methanol to methyl acrylate. Alternatively, acrolein can be oxidized to acrylic acid, as outlined in U.S. Pat. No. 4,892,856.

In another alternative, acetaldehyde from the dehydration of ethylene glycol can be supplemented with acetaldehyde from ethanol (through a catalytic dehydrogenation, for example), and the acetaldehyde feed converted to methyl acrylate or acrylic acid. Alternatively, the acetaldehyde may be subjected to base-catalyzed aldol condensation with formaldehyde to form 3-hydroxypropanal, which rearranges to form acrolein. Acrolein can then be converted through reaction with methanol to methyl acrylate. Alternatively, the acrolein can be oxidized to acrylic acid.

Those skilled in the art will appreciate that such supplemental biobased aldehydes may also be obtained by other means, for example, fusel oil may be used to produce a mixture of aldehydes which can be combined with the aldehydes from a biobased EG, PG, or mixed alkylene glycols feed. Fusel oil, an unwanted by-product of ethanol fermentation or sulfite waste liquor, is in this respect a waste stream of little commercial value, often disposed of by being bled off into fuel alcohol for blending with gasoline. This fusel oil (also called fusel alcohols or potato oil) often comprises alcohols having three or more carbon atoms, such as 1-propanol, 2-propanol, amyl alcohol, and isomers of butanol, and these may be subjected to catalytic oxidation to produce the abovementioned mixture of aldehydes. Alternatively, fusel oil can be combined with EG, PG, or a mixed alkylene glycols feed and subjected to catalytic oxidation to provide a stream of mixed aldehydes. The resulting mixtures of aldehydes may be subjected to hydroformylation to form mixed unsaturated aldehydes, which may be subjected to oxidation to form mixed unsaturated acids or oxidized in the presence of methanol to form methyl esters of unsaturated aldehydes.

Acrylic acid compositions may be made using acrylic acid monomers made from one or more alkylene glycols as just described. It is noted that these compositions can be formulated in all respects in a conventional manner, so that a biobased acrylic acid made from a bioderived propylene glycol, for example, can be treated as a direct, renewably-sourced substitute for an acrylic acid that derives from propylene obtained from petroleum processing.

For example, acrylic acid obtainable by the processes we've described can equally be a starting material for the manufacture of acrylic esters, as well as for polyacrylic acid and salts thereof useful as thickeners, dispersants and rheology controllers. Acrylic acid obtainable by the processes we've described can also be used in the place of conventionally-derived acrylic acid, in the manufacture of polyacrylates. Polyacrylates, which account for a major portion of world usage of acrylic acid, are used for superabsorbent polymers, widely used in hygiene products, such as diapers (nappies), and soaker pads in food packaging. Due to the disposable nature of most superabsorbent polymer applications, superabsorbent polymers made from biobased acrylic acid should offer substantial benefits related to global carbon balances.

Still other end uses and applications may be contemplated. For example, when combined with acrylamide, a flocculent containing renewably-based acrylic acid can be obtained, while copolymerization yields anionic polyacrylamide and hydroxyacrylates for use in industrial coating formulations. When combined with ethylene, ion exchange polymers containing renewably-based acrylic acid can be obtained. Further uses can be identified in the fields of plastics, paper manufacture and coating, exterior house paints for wood and masonry, interior wall paints, coatings for compressed board and related building materials, flocculation of mineral ore fines and waste water, treatment of sewage, printing inks, floor polishes, floor and wall coverings, industrial primers, textile sizing, treatment and finishing, leather impregnation and finishing, masonry sealers, lubricating and fuel oil additives, lacquers for automotive, appliance and furniture finishes, pharmaceutical binders, and hot metal coatings. Preferably the acrylic acid compositions of the present invention will include substantially only renewably-based or biobased components.

Alkylene glycol-based methyl methacrylate compositions can likewise be prepared in all respects in a conventional manner, as compositions including or deriving from conventionally produced methyl methacrylate. For example, methyl methacrylate made by a method as described herein can be used in the manufacture of polymethyl methacrylate acrylic plastics (PMMA), useful as light, shatter-resistant alternatives to glass such as Plexiglas™. In addition, alkylene glycol-based methyl methacrylate can be used in manufacture of the PVC modifier methyl methacrylate-butadiene-styrene (MBS) copolymers. Preferably the methyl methacrylate compositions including alkylene glycol-based methyl methacrylate will include substantially only renewably-based or biobased components.

Compositions using a mixture of alkylene glycol-based alkyl acrylate and alkyl methacrylate materials can be prepared and used also, in the same manner as equivalent alkyl acrylate and alkyl methacrylate compositions based on, including or deriving from conventionally produced alkyl acrylate and alkyl methacrylate materials.

Production of acrylic acid and methyl methacrylate from propylene glycol and mixtures of acrylic acid and methacrylic acid from mixtures of ethylene glycol and propylene glycol is illustrated more particularly by the following, non-limiting examples:

EXAMPLE 1

A 3-neck flask equipped with a vigreux column, a Dean-Stark trap and reflux condenser was charged with propylene glycol (700 g) and sulfuric acid (5% w/w 19.02 mL). The solution was stirred using a magnetic stirrer and heated to 145° C. The reaction mixture began to reflux at 145° C. After refluxing the reaction for 120 minutes the reaction mixture was cooled and analyzed by GC-MS. The presence of propanal was confirmed by GC-MS. The formation of 2-ethyl-4-methyl-1,3-dioxolane, which contained propanal trapped a cyclic acetal with propylene glycol, was also confirmed (FIG. 2).

EXAMPLE 2

Figure 4:
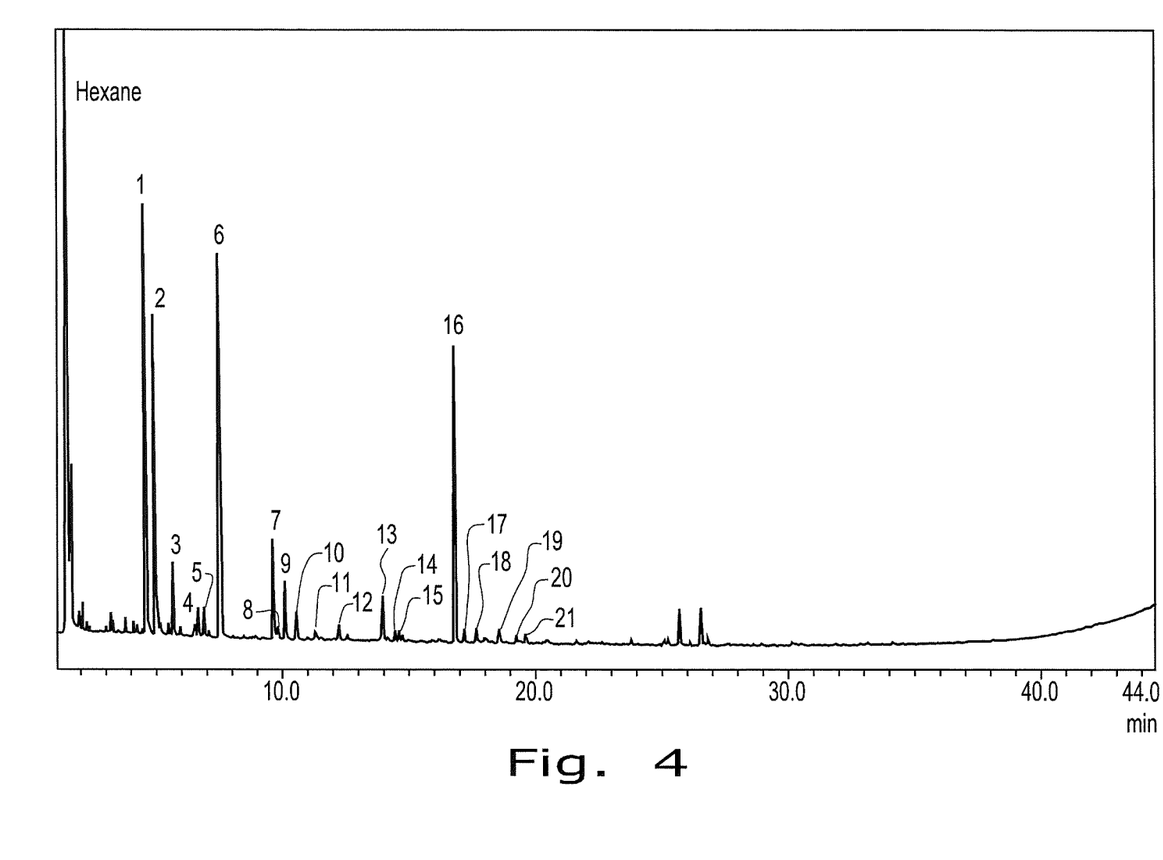
FIG. 4 presents a GC-MS chromatogram of the top layer formed in Example 2B. Peaks 1 and 2 are 4-methyl-2-ethyl-1,3-dioxolane.

A 1 liter autoclave reactor was charged with 400 g of propylene glycol and 4 g of sulfuric acid (1% w/w). The reactor system was assembled, pressurized to 500 psi with argon and heated to 200° C. The reactor was maintained at 200° C. for 5 hours, reaching a pressure of 1000 psi, then cooled to room temperature. The reaction mixture was transferred to a 1 L glass bottle. The product mixture comprised two layers. The bottom layer was grey in color and looked like an aqueous product and the top layer was brown in color and looked like a non-aqueous product. Weight of the top layer was 142.39 grams, and the weight of the bottom layer was 244.59 grams. The two layers were separated and an aliquot from each layer was submitted for analysis. The formation of propanal trapped in 4-methyl-2-ethyl-1,3-dioxolane was confirmed in the GC-MS analysis (FIG. 3, bottom layer; peaks 3 and 4; FIG. 4, top layer; peaks 1 & 2).

EXAMPLE 3

A 1 L Autoclave engineer reactor was charged with 400 g propylene glycol and 15.3 g of trifluoroacetic acid (3.8% w/w). The reactor system was assembled and heated to 200° C. The reactor was maintained at this temperature for 5 h and then cooled to room temperature. GC-MS analysis confirmed the formation of propanal trapped in 4-methyl-2-ethyl-1,3-dioxolane.

EXAMPLE 4

A 1 L Autoclave engineer reactor was charged with 400 g propylene glycol and 4 g of methanesulfonic acid (1% w/w). The reactor system was assembled, pressurized to 500 psi with argon and heated to 200° C. The reactor was maintained at this temperature for 5 h, reaching a pressure of 750 psi, and then cooled to room temperature. The product mixture was dark brown in color, with a small amount of organic layer on the top. GC-MS analysis confirmed the formation of propanal trapped in 1,1 dimethoxypropane and in 4-methyl-2-ethyl-1, 3-dioxolane.

EXAMPLE 5

Tungstated zirconia (XZO1250, Batch no PRB738, MEL chemicals, Flemington, N.J., 20 g) acid catalyst was activated in a tube furnace at 650° C. (ramped at 5° C./min to 700° C.) for 4 hours. The activated catalyst was cooled to 250° C. and added to 400 g of propylene glycol. A 1 L autoclave engineer reactor was charged with this mixture. The reactor was assembled and heated to 180° C. The reactor was maintained at this temperature for 5 hours. The reactor was cooled and the contents were transferred to 1 L glass bottle. A aliquot of this mixture was analyzed by GC-MS, which confirmed the formation of propanal trapped in 4-methyl-2-ethyl-1,3 dioxolane.

What is claimed is:

1. A process comprising dehydrating a mixture of ethylene and propylene glycols to form a mixed aldehydes dehydration product, combining mixed aldehydes from dehydrating the ethylene and propylene glycols with formaldehyde through aldol condensation to yield a mixed acrolein and methacrolein product, and then oxidizing the mixed acrolein and methacrolein product to provide a mixture of acrylic and methacrylic acids.

2. A process as in claim 1, further comprising esterifying the mixture of acrylic and methacrylic acids to provide a mixed acrylic acid ester and methacrylic acid ester product.

3. A process as in claim 2, wherein the esterification is with methanol and a mixed methacrylate and methyl methacrylate product results.

4. A process as in claim 3, further comprising combining the mixed methacrylate and methyl methacrylate product with an organic compound capable of copolymerization with methacrylate and methyl methacrylate.

5. A process as in claim 4, further comprising adding an organic peroxide and an activator and causing a polymerization reaction to occur.

6. A process as in claim 3, further comprising subjecting the mixed methacrylate and methyl methacrylate product to anionic polymerization with a core-forming monomer to provide a lubricating oil additive polymer.

7. A process as in claim 1, claim 2, claim 3, claim 4, claim 5 or claim 6, wherein the mixture of ethylene and propylene glycols derives at least in part from the hydrogenolysis of one or more polyols, glycerol, sorbitol, and lactic acid to a mixed glycols composition inclusive of ethylene glycol and propylene glycol.

* * * * *